(12) United States Patent
Kim et al.

(10) Patent No.: US 11,759,407 B2
(45) Date of Patent: *Sep. 19, 2023

(54) COMPOSITION FOR SKIN WHITENING OR WOUND TREATMENT, CONTAINING LIQUID PLASMA

(71) Applicant: AJOU UNIVERSITY INDUSTRY-ACADEMIC COOPERATION FOUNDATION, Gyeonggi-do (KR)

(72) Inventors: Chul Ho Kim, Seoul (KR); Sung Un Kang, Gyeonggi-do (KR)

(73) Assignee: AJOU UNIV. INDUSTRY-ACADEMIC COOPERATION FOUND., Gyeonggi-do (KR)

( * ) Notice: Subject to any disclaimer, the term of this patent is extended or adjusted under 35 U.S.C. 154(b) by 109 days.

This patent is subject to a terminal disclaimer.

(21) Appl. No.: 16/464,180

(22) PCT Filed: Nov. 13, 2017

(86) PCT No.: PCT/KR2017/012771
§ 371 (c)(1),
(2) Date: May 24, 2019

(87) PCT Pub. No.: WO2018/097527
PCT Pub. Date: May 31, 2018

(65) Prior Publication Data
US 2020/0129386 A1    Apr. 30, 2020

(30) Foreign Application Priority Data

Nov. 25, 2016 (KR) .................. 10-2016-0158673
Nov. 25, 2016 (KR) .................. 10-2016-0158678
Aug. 31, 2017 (KR) .................. 10-2017-0110760
Aug. 31, 2017 (KR) .................. 10-2017-0110761

(51) Int. Cl.
| | |
|---|---|
| A61B 18/00 | (2006.01) |
| A61K 8/02 | (2006.01) |
| A61K 8/64 | (2006.01) |
| A61K 8/22 | (2006.01) |
| A61K 38/18 | (2006.01) |
| A61P 17/02 | (2006.01) |
| A61K 47/02 | (2006.01) |
| A61Q 19/02 | (2006.01) |

(52) U.S. Cl.
CPC .............. *A61K 8/0204* (2013.01); *A61K 8/22* (2013.01); *A61K 8/64* (2013.01); *A61K 38/1808* (2013.01); *A61K 38/1825* (2013.01); *A61K 38/1841* (2013.01); *A61K 38/1858* (2013.01); *A61K 47/02* (2013.01); *A61P 17/02* (2018.01); *A61Q 19/02* (2013.01)

(58) Field of Classification Search
CPC . A61B 18/04; A61B 18/042; A61B 2018/042; A61B 2018/044; A61B 2018/046; A61B 2018/048
See application file for complete search history.

(56) References Cited

U.S. PATENT DOCUMENTS

| | | | |
|---|---|---|---|
| 5,876,663 A | 3/1999 | Laroussi | |
| 6,518,538 B2 | 2/2003 | Bernabei | |
| 9,226,790 B2 | 1/2016 | Zemel et al. | |
| 11,246,885 B2* | 2/2022 | Kim | ................... A61N 1/44 |
| 2007/0213700 A1* | 9/2007 | Davison | ............ A61B 18/1402 606/32 |
| 2008/0119781 A1 | 5/2008 | King | |
| 2012/0089084 A1* | 4/2012 | O'Keeffe | ............ A61L 26/0057 523/105 |
| 2013/0345620 A1* | 12/2013 | Zemel | ................. A61B 18/042 604/24 |
| 2014/0377320 A1* | 12/2014 | Pietramaggiori | ....... A61L 27/28 424/422 |
| 2016/0071905 A1* | 3/2016 | Park | ........................ G06F 3/061 711/104 |
| 2016/0296763 A1* | 10/2016 | Kim | ........................ H05H 1/24 |
| 2020/0254008 A1 | 8/2020 | Kim et al. | |

FOREIGN PATENT DOCUMENTS

| | | |
|---|---|---|
| JP | 10-286316 | 10/1998 |
| JP | 2014-212839 | 11/2014 |

(Continued)

OTHER PUBLICATIONS

Mohades etal (Temporal evaluation of the anti-tumor efficiency of plasma-activated media; Plasma Process Polym, 2016; 13: 1206-1211) (Year: 2016).*

(Continued)

*Primary Examiner* — Micah Paul Young
(74) *Attorney, Agent, or Firm* — MORRISON & FOERSTER LLP

(57) ABSTRACT

The present invention relates to a composition for skin whitening or wound treatment including liquid-type plasma, and more particularly, to a cosmetic composition for skin whitening and a pharmaceutical composition for treating and preventing skin pigmentation diseases which contain liquid-type plasma as an active ingredient. In addition, the present invention relates to a pharmaceutical composition for wound treatment, a quasi-drug composition, and a health functional food composition, which include liquid-type plasma and a growth factor as active ingredients, and a wound treatment method including a step of administering the composition to a subject or a step of applying the composition on the skin. The composition including liquid-type plasma and a growth factor of the present invention is capable of inducing the proliferation of fibroblasts, thereby exhibiting excellent wound treatment efficacy. Accordingly, the composition including liquid-type plasma and a growth factor of the present invention can be usefully applied to medicines including external preparations for wound treatment, etc.

7 Claims, 11 Drawing Sheets

(56) References Cited

FOREIGN PATENT DOCUMENTS

| KR | 10-0509848 | 4/2004 | | |
|---|---|---|---|---|
| KR | 10-0479741 | 3/2005 | | |
| KR | 10-1101321 | 5/2010 | | |
| KR | 10-2012-0039199 | 4/2012 | | |
| KR | 10-1568380 | 11/2015 | | |
| KR | 10-1635718 | 7/2016 | | |
| KR | 10-1657063 | 9/2016 | | |
| WO | WO 2015/191843 | 12/2015 | | |
| WO | WO-2015191843 A1 | * | 12/2015 | ............ A61P 31/04 |
| WO | WO 2016/167516 | 10/2016 | | |

OTHER PUBLICATIONS

Emmert et al (Atmospheric pressure plasma in dermatology: Ulcus treatment and much more; Clinical Plasma Medicine, 1, 2013, 24-29). (Year: 2013).*

Heinlin et al (Plasma medicine: possible applications in dermatology, JDDG, 12, 2010). (Year: 2010).*

Kang et al., "N2 non-thermal atmospheric pressure plasma promotes wound healing in vitro and in vivo: Potential modulation of adhesion molecules and matrix metalloproteinase-9." Experimental Dermatology (2017) 26:163-170.

Lee et al., "Nonthermal Plasma Induces Apoptosis in ATC Cells: Involvement of JNK and p38 MAPK-Dependent ROS," Yonsei Med J (2014) 55(6):1640-1647.

Kubinova et al., "Non-thermal Air Plasma Promotes the Healing of Acute Skin Wounds in Rats," Sci Rep (2017) 7: 45183, 11 pages.

Lee et al., "Suppression of scar formation in a murine A23burn wound model by the application of non-thermal plasma," Appl. Phys. Lett. (2011) 99: 203701.

Sato et al., "Successful Use of Argon Plasma Coagulation and Tranilastto Treat Granulation Tissue Obstructing the Airway After Tracheal Anastomosis," Chest (2000) 118 (6), 1829-1831.

Sharma, Effects of Cold Atmospheric Pressure Plasma Jet on the Viability of Bacillus subtilis Endospores, 2013, gair.media.gurima-u.ac.jp/dspace/bitstream/10087/7661/1IThesis%2ofor%2oDoctor%200f%2oEngineeririg%20(VinitaSharma).pdf Year: 2013).

Ahn et al., "Targeting Cancer Cells with Reactive Oxygen and Nitrogen Species Generated by Atmospheric-Pressure Air Plasma," PLoS ONE 9(1): e86173.

* cited by examiner

COMPOSITION FOR SKIN WHITENING OR WOUND TREATMENT, CONTAINING LIQUID PLASMA

STATEMENT OF GOVERNMENTAL SUPPORT

The invention was made with government support under Serial No. 2017M3A9F7079339 awarded by Ministry of Science and ICT (Republic of Korea), Serial No. P0004089 awarded by Ministry of Trade, Industry and Energy (Republic of Korea), and Serial No. 2018-JB-RD-0006 awarded by Ministry of Science and ICT (Republic of Korea). This application was also supported by the Ministry of Health and Welfare (No. HR21C1003 (1465034377)).

CROSS REFERENCE TO RELATED APPLICATIONS

This application is a national stage application under 35 U.S.C. § 371 of International Application No. PCT/KR2017/012771, filed internationally on 13 Nov. 2017, which claims priority to Korean Application No. 10-2016-0158673, filed 25 Nov. 2016; Korean Application No. 10-2016-0158678, filed 25 Nov. 2016; Korean Application No. 10-2017-0110760, filed 31 Aug. 2017; and, Korean Application No. 10-2017-0110761, filed 31 Aug. 2017. The contents of the above patent applications are incorporated by reference herein in their entirety.

TECHNICAL FIELD

The present invention relates to a composition for skin whitening or wound treatment including liquid-type plasma, and more particularly, to a cosmetic composition for skin whitening and a pharmaceutical composition for treating and preventing skin pigmentation diseases which contain liquid-type plasma as an active ingredient. In addition, the present invention relates to a pharmaceutical composition for wound treatment, a quasi-drug composition, and a health functional food composition, which include liquid-type plasma and a growth factor as active ingredients, and a wound treatment method including a step of administering the composition to a subject or a step of applying the composition on the skin. The composition including liquid-type plasma and a growth factor of the present invention is capable of inducing proliferation of fibroblasts, thereby exhibiting excellent wound treatment efficacy. Accordingly, the composition including liquid-type plasma and a growth factor of the present invention is usefully applicable to medicines including external preparations for wound treatment, etc.

BACKGROUND ART

Melanogenesis is a result of an increase in melanin production activity as a defense mechanism of melanin-producing cells (melanocytes) against stimuli such as ultraviolet light and, accordingly, a large amount of melanin, produced by the increased melanin production activity, is transferred to keratinocytes. Although melanin protects the skin, hyperpigmentation of the skin causes melasma, freckles, melanogenesis after inflammation of the skin, senile lentigo, and the like. This may have negative effects on appearance and metal health and thus may have negative effects on social activities. Melanin is produced through non-enzymatic oxidation after an enzyme called tyrosinase acts on tyrosine as a type of an amino acid to be converted into DOPA or dopaquinone. It is known that excessive deposition of such melanin causes generation of freckles, age spots, etc. As materials for inhibiting the generation of melanin to alleviate, prevent, and treat such pigmentation, freckles, spots, etc., for example, hydroquinone, arbutin, vitamin C, and derivatives thereof have been developed. Whitening cosmetics containing such materials have been disclosed. Korean Patent Publication No. 2005-0509848 discloses a whitening cosmetic containing a khellactone derivative isolated from Anthriscus sylvestris Hoffm. In addition, Korean Patent Publication No. 2005-0479741a discloses a whitening cosmetic containing a glucose acylated derivative. As hydroquinone of the materials is recognized as effective, use thereof is limited due to sensitivity thereof. Since ascorbic acid is easily oxidized, a cosmetic mixed with ascorbic acid may cause discoloration and odor changes. Since the efficacy of substances derived from plant extracts greatly depends on the origins thereof, it is difficult to maintain the homogeneity of products produced from the substances. In the case of glucose acylated derivatives, synthesis efficiency thereof is very low.

Meanwhile, the skin acts as a protective barrier of the body and is the body's primary line of defense against diseases. The skin epidermis is a barrier against microbial invasion. Accordingly, a primary objective in treatment of wounds, burns, abrasions and other types of damage to the skin is rapid closure and wound healing to prevent infection. Wound healing is a complex process generally involving three stages of inflammation, proliferation, and remodeling. The first step involves clotting to accomplish hemostasis and neutrophil replacement to destroy bacteria and necrotic tissue, followed by supplementation of macrophages. During the second step, angiogenesis occurs. At this time, fibroblasts enter a wound site while endothelial cells enter the wound site, which helps to produce granulation tissue. The granulation tissue production allows re-epithelialization. During the final step, the levels of collagen production and destruction become equal, and healed wounds are slowly changed to achieve maximum strength. Such wound healing is delayed or impaired when any one of the steps is not performed in an appropriate or timely fashion. This may cause chronic wounds which are not only important problems for individuals but also costly clinical problems.

Wound healing (wound closure), which refers to clinically complete closure of the skin, is a complex process wherein various cell types such as keratinocytes, fibroblasts, endothelial cells, macrophages, and platelets interact and are controlled. Respective steps of the process are controlled by a complex signaling network which is regulated by various growth factors, cytokines, and chemokines.

Wounds should be quickly treated to reduce the risk of secondary infection. In addition, normal wound healing is delayed due to lack of progression from an inflammatory stage to a proliferative stage when inflammation continues in a wound treatment process. For this reason, development of a wound treatment method not inducing inflammation is actively underway.

The applicants of the present invention have completed the present invention to address the problems. The present invention relates to a composition for skin whitening or wound treatment including liquid-type plasma. The present inventors have made intensive efforts to develop a fundamental method of treating skin pigmentation. As a result, the present inventors have found that liquid-type plasma has inhibitory effects on tyrosinase activity and melanin biosynthesis and, accordingly, can be used for skin whitening. In addition, the present inventors have made intensive efforts to develop a fundamental wound treatment method. As a result, the present inventors have found that regeneration of fibroblasts is promoted when the fibroblasts are treated with liquid-type plasma and an epidermal growth factor (EGF), thus completing the present invention.

RELATED ART DOCUMENT

1. International Patent Laid-Open Publication No. WO2016167516

DISCLOSURE

Technical Problem

Therefore, the present invention has been made in view of the above problems, and it is one object of the present invention to provide a composition for skin whitening or wound treatment including liquid-type plasma.

It will be understood that technical problems of the present invention are not limited to the aforementioned problem and other technical problems not referred to herein will be clearly understood by those skilled in the art from the description below.

Technical Solution

Hereinafter, various embodiments described herein will be described with reference to the accompanying drawings. In the following description, for complete understanding of the present invention, various specific details, e.g., such as specific forms, compositions, processes, and the like, are described. However, certain embodiments may be implemented without one or more of these specific details or with other known methods and forms. In other embodiments, well-known process and manufacturing techniques are not described in specific forms, in order not to unnecessarily obscure the present invention. References throughout the specification for "one embodiment" or "an embodiment" mean that particular features, forms, compositions, or characteristics disclosed in connection with the embodiment are included in one or more embodiments of the present invention. Accordingly, "one embodiment" or "an embodiment" expressed in various parts throughout this specification does not necessarily represent the same embodiment of the present invention. Additionally, particular features, forms, compositions, or characteristics may be combined in any suitable manner in one or more embodiments.

One objective of the present invention provides a composition for skin whitening including liquid-type plasma that exhibits excellent whitening effect, due to a tyrosinase activity inhibition effect and a melanin biosynthesis inhibition effect, and excellent stability.

Another objective of the present invention provides a cosmetic composition for skin whitening containing the composition for skin whitening including liquid-type plasma.

Still another objective of the present invention provides a pharmaceutical composition for treating or preventing hyperpigmentation disorders containing the composition for skin whitening including plasma.

Yet another objective of the present invention provides a pharmaceutical composition for wound treatment including liquid-type plasma and a growth factor as active ingredients.

Yet another objective of the present invention provides a quasi-drug composition for wound treatment including liquid-type plasma and a growth factor as active ingredients.

Yet another objective of the present invention provides a health functional food composition for wound treatment including liquid-type plasma and a growth factor as active ingredients.

Yet another objective of the present invention provides a wound treatment method including a step of administering the composition including liquid-type plasma and a growth factor, as active ingredients, to a subject.

Yet another objective of the present invention provides a wound treatment method including a step of applying the composition including liquid-type plasma and a growth factor, as active ingredients, on the skin.

In this specification, the term "liquid-type plasma (non-thermal plasma-treated solution, NTS)" refers to high-density, high energy plasma generated in a liquid. The liquid-type plasma may be prepared by exposure to nonthermal plasma (NTP) at atmospheric pressure. The term "liquid-type plasma" may be interchangeably used with the term "plasma-conditioned liquid material." The "liquid material" may be any liquid-type material without specific limitation, but is preferably water, saline, buffer, or a culture medium, and most preferably a culture medium.

The term "culture medium" used in the present specification refers to a culture medium allowing cell growth and survival in vitro and includes all of general used culture media in the art suitable for cell culture. A culture medium and a culturing condition may be selected according to cell type. A basic culture medium used for cell culture is preferably a cell culture minimum medium (CCMM) and generally includes a carbon source, a nitrogen source, and trace element components. Examples of such a basic cell culture medium include, for example, Dulbecco's Modified Eagle's Medium (DMEM), Minimal essential Medium (MEM), Basal Medium Eagle (BME), RPMI1640, F-10, F-12, Glasgow's Minimal essential Medium (GMEM), Iscove's Modified Dulbecco's Medium, and the like, but the present invention is not limited thereto.

The term "whitening" used in the present specification refers to a function of preventing an increase of melanin cells due to continuous exposure of the skin to ultraviolet light and, accordingly, excessive deposition of a melanin pigment in the skin, or thinning a previously deposited melanin pigment. Accordingly, the generation of melasma or freckles caused by excessive deposition of a melanin pigment may be prevented.

The term "growth factor" used in the present specification refers to a polypeptide that promotes division, growth, and differentiation of various cells. Examples of a growth factor include an epidermal growth factor (EGF), platelet-derived growth factor-AA (PDGF-AA), insulin-like growth factor-1 (IGF-1), transforming growth factor-β (TGF-β), and a fibroblast growth factor (FGF), but the present invention is not limited thereto.

In an embodiment of the present invention, "treatment" refers to any actions of alleviating or beneficially altering skin pigmentation, wounds, and other conditions associated with skin pigmentation and wounds using the liquid-type plasma according to the present invention. Those skilled in the art will be able to ascertain the precise criteria for skin pigmentation and to determine the degree of alleviation, reduction, and treatment of skin pigmentation based on data presented by the Korean Medical Association.

In an embodiment of the present invention, "prevention" refers to any actions of inhibiting or delaying skin pigmentation, wounds, and other symptoms associated with skin pigmentation and wounds using the liquid-type plasma according to the present invention. It will be apparent to those skilled in the art that the composition including the liquid-type plasma according to the present invention having therapeutic effects on skin pigmentation diseases or wounds may be used to prevent skin pigmentation or wounds before initial symptoms or symptoms of skin pigmentation or wounds appear.

In the present specification, "pharmaceutical composition" refers to a composition administered for a specific purpose. For the objects of the present invention, the pharmaceutical composition of the present invention includes liquid-type plasma, prepared injecting plasma into a liquid material, as an active ingredient. In addition, the pharmaceutical composition may include a relevant protein and pharmaceutically acceptable carrier, excipient, or diluent. The term "pharmaceutically acceptable" carrier or excipient are those approved by the regulatory authorities of the government or listed in government or other generally approved pharmacopoeias for use in vertebrates and more particularly in humans.

For parenteral administration, the pharmaceutical composition of the present invention may be in the form of a suspension, solution or emulsion in an oily or aqueous carrier, and may be prepared in the form of a solid or semi-solid. In addition, the pharmaceutical composition of the present invention may contain formulatory agents such as suspending, stabilizing, solubilizing and/or dispersing agents and may be sterilized. The pharmaceutical composition may be stable under preparation and storage conditions and may be preserved against contaminating actions of microorganisms such as bacteria or fungi. Alternatively, the pharmaceutical composition of the present invention may be in the form of a sterile powder for reconstitution with a proper carrier prior to use. The pharmaceutical composition may be in unit-dose form or in a micro needle patch form, or may be contained in an ampoule, in other unit-dose containers, or in multi-dose containers. Alternatively, the pharmaceutical composition may be stored in a freeze-dried (lyophilized) state requiring only the addition of a sterile liquid carrier, e.g., the addition of water for injection, immediately prior to use. Immediate injection solutions and suspensions may be prepared from sterile powders, granules or tablets.

In some non-limiting embodiments, the pharmaceutical composition of the present invention may be formulated and included in the form of microspheres in a liquid. In certain non-limiting embodiments, the pharmaceutical composition of the present invention may contain pharmaceutically acceptable compounds and/or a mixture thereof at a concentration of 0.001 to 100,000 U/kg. In addition, in certain non-limiting embodiments, the pharmaceutical composition of the present invention may include suitable excipients such as a preservative, a suspending agent, an additional stabilizer, a dye, a buffer, an antimicrobial agent, an antifungal agent, and an isotonic agent, e.g., sugar or sodium chloride. The term "stabilizer" used in the present specification refers to a compound selectively used in the pharmaceutical composition of the present invention to increase shelf life. In a non-limiting embodiment, the stabilizer may be a sugar, an amino acid, or a polymer. In addition, the pharmaceutical composition of the present invention may include one or more pharmaceutically acceptable carriers. Here, the carriers may be solvents or dispersed culture media. Non-limiting examples of the pharmaceutically acceptable carriers include water, saline, ethanol, polyols (e.g., glycerol, propylene glycol, and liquid polyethylene glycol), an oil, and a suitable mixture thereof. Non-limiting examples of sterilization techniques applied to the pharmaceutical composition of the present invention include filtration through a bacteria-inhibiting filter, terminal sterilization, incorporation of a sterile preparation, irradiation, irradiation with sterilization gas, heating, vacuum drying, and freeze-drying.

In the present specification, "administration" refers to a process of introducing the composition of the present invention to a patient in any suitable manner. The composition of the present invention may be administered through any conventional route to be applied to a target tissue. The pharmaceutical composition of the present invention may be administered orally, intraperitoneally, intravenously, intramuscularly, subcutaneously, intradermally, intranasally, intrapulmonaryly, intrarectally, intravitreally, intraperitoneally, or intradurally, most preferably is provided in the form of being applied on the skin or injected subcutaneously or intradermally, but the present invention is not limited thereto.

A treatment method according to the present invention may include administering the pharmaceutical composition in a pharmaceutically effective amount. In the present invention, an effective amount may be controlled according to various factors such as disease type, the severity of disease, the type and content of active and other ingredients contained in a composition, formulation type, the age, body weight, general health status, sex and diet of a patient, the time and route of administration, secretion rate of a composition, and co-administered drug types.

In the present specification, the term "cosmetic composition" refers to a composition for alleviating or reducing skin pigmentation, wounds, and other symptoms such as skin pigmentation and wounds. A cosmetic composition including the composition of the present invention as an active ingredient may be prepared in the form of a tonic, a nutrition lotion, a nutritional essence, a massage cream, a beauty bath additive, a body lotion, a body milk, a bath oil, a baby oil, a baby powder, a shower gel, a shower cream, a sunscreen lotion, a sunscreen cream, a suntan cream, a skin lotion, a skin cream, ultraviolet light blocking cosmetics, a cleansing milk, a depilatory (for makeup), a face and body lotion, a face and body cream, a skin whitening cream, a hand lotion, a hair lotion, a cosmetic cream, a jasmine oil, a bath soap, a water soap, a soap, a shampoo, a hand cleanser, a medicinal soap (non-medical soap), a cream soap, a facial wash, a hair rinse, a cosmetic soap, a tooth whitening gel, a toothpaste, or the like. For this, the composition of the present invention may further include a suitable carrier, excipient, or diluent generally used to prepare a cosmetic composition. Examples of a carrier, excipient, or diluent that may be further included in the cosmetic composition of the present invention include purified water, an oil, a wax, fatty acids, fatty alcohols, fatty acid esters, a surfactant, a humectant, a thickener, an antioxidant, a viscosity stabilizer, a chelating agent, a buffer, lower alcohols, and the like, but the present invention is not limited thereto. In addition, a whitening agent, a moisturizing agent, vitamins, a sunscreen agent, a perfume, a dye, antibiotics, an antibacterial agent, and an antifungal agent may be included as needed. Examples of the oil include hydrogenated vegetable oil, castor oil, cottonseed oil, olive oil, palm oil, jojoba oil, and avocado oil. Examples of the wax include yellow beeswax, hard wax, carnauba, candelilla, montan, ceresin, liquid paraffin, and lanolin. Stearic acid, linoleic acid, linolenic acid, and oleic acid may be used as the fatty acid; cetyl alcohol, octyl dodecanol, oleyl alcohol, panthenol, lanolin alcohol, stearyl alcohol, and hexadecanol may be used as the fatty acid alcohols; and isopropyl myristate, isopropyl palmitate, and butyl stearate may be used as the fatty acid ester. As the surfactant, a cationic surfactant, an anionic surfactant, and a nonionic surfactant known in the art may be used. Thereamong, a surfactant derived from a natural material is preferred. In addition, a moisture absorbent, a thickener, an antioxidant, and the like, which are well known in the cosmetics field, may be included and the types and amounts thereof may be determined as known in the art.

An embodiment of the present invention provides a method of preparing liquid-type plasma including (a) a step of filling a plasma generator with a carrier gas; (b) a step of supplying a voltage of 0.5 kV to 20 kV and a frequency of 10 to 30 kHz to the plasma generator to generate plasma; and (c) a step of irradiating a liquid material with the generated plasma. In step (a), the carrier gas may be one or more selected from the group consisting of nitrogen, helium, argon, and oxygen. In step (c), the liquid material is water, saline, a buffer, or a culture medium.

In another embodiment of the present invention, liquid-type plasma composition including liquid-type plasma prepared according to one or more steps of the method is provided.

In still another embodiment of the present invention, a pharmaceutical composition for preventing or treating skin pigmentation diseases including the liquid-type plasma composition as an active ingredient is provided. Here, the skin pigmentation diseases may be one or more selected from the group consisting of melasma, freckles, a lentigo, a nevus, drug-induced pigmentation, post-inflammatory pigmentation, and hyperpigmentation caused by dermatitis.

Yet another embodiment of the present invention provides a method of preventing or treating skin pigmentation diseases, the method including a step of administering the pharmaceutical composition to a subject, Here, the skin pigmentation diseases may be one or more selected from the group consisting of melasma, freckles, a lentigo, a nevus, drug-induced pigmentation, post-inflammatory pigmentation, and hyperpigmentation caused by dermatitis.

In yet another embodiment of the present invention, a use of the pharmaceutical composition for preventing or treating skin pigmentation diseases is provided.

In yet another embodiment of the present invention, a cosmetic composition for skin whitening including the liquid-type plasma composition as an active ingredient is provided.

In yet another embodiment of the present invention, a pharmaceutical composition for wound treatment including the liquid-type plasma composition as an active ingredient is provided. The pharmaceutical composition may further include a growth factor. The growth factor may be an epidermal growth factor (EGF), platelet-derived growth factor-AA (PDGF-AA), insulin-like growth factor-1 (IGF-1), transforming growth factor-$\beta$ (TGF-$\beta$), or a fibroblast growth factor (FGF). The wound may be a puncture wound, decortication, a rash, inflammation, an ulcer, or a skin injury due to scratches.

In yet another embodiment of the present invention, a wound treatment method including a step of administering the pharmaceutical composition to a subject is provided. The wound may be a puncture wound, decortication, a rash, inflammation, an ulcer, or a skin injury due to scratches.

In yet another embodiment of the present invention, a use of the pharmaceutical composition for wound treatment is provided.

In yet another embodiment of the present invention, a quasi-drug composition for wound treatment including the liquid-type plasma composition as an active ingredient is provided. The quasi-drug composition may further include a growth factor. The growth factor may be an epidermal growth factor (EGF), platelet-derived growth factor-AA (PDGF-AA), insulin-like growth factor-1 (IGF-1), transforming growth factor-$\beta$ (TGF-$\beta$), or a fibroblast growth factor (FGF).

Hereinafter, the respective steps of the present invention are described in detail.

Advantageous Effects

A cosmetic composition for skin whitening or a composition for treating or preventing hyperpigmentation disorders including liquid-type plasma according to the present invention exhibits an excellent tyrosinase activity inhibition effect and an excellent melanin biosynthesis inhibition effect. Accordingly, it is anticipated that the liquid-type plasma according to the present invention can be usefully applied to a cosmetic composition for whitening or a pharmaceutical composition for treating and preventing skin pigmentation diseases. In addition, a composition including the liquid-type plasma according to the present invention and a growth factor can promote the regeneration of fibroblasts. Therefore, it is anticipated that the composition including the liquid-type plasma and the growth factor according to the present invention can promote wound healing.

BEST MODE FOR CARRYING OUT THE INVENTION

Human foreskin tissue was cultured in Transwell (DMEM high glucose+4% FBS), and then treated with liquid-type plasma at a rate of 1 min/1 ml. After 3 days of culturing, the tissue was fixed and a pigmentation degree thereof was observed through Fontana-Masson staining. As a result, it was confirmed that epidermal staining in the human skin tissue treated with the liquid-type plasma was weaker than that in a control.

MODE FOR CARRYING OUT THE INVENTION

Hereinafter, the present invention will be described in more detail with reference to the following Examples. It will be apparent to those skilled in the art that the Examples are merely for concretely explaining the invention and therefore, there is no intent to limit the invention to the Examples.

Example 1. Preparation of Liquid-Type Plasma

Example 1-1. Preparation of Liquid-Type Plasma (Nonthermal Plasma-Treated Solution, NTS)

Figure 1A:
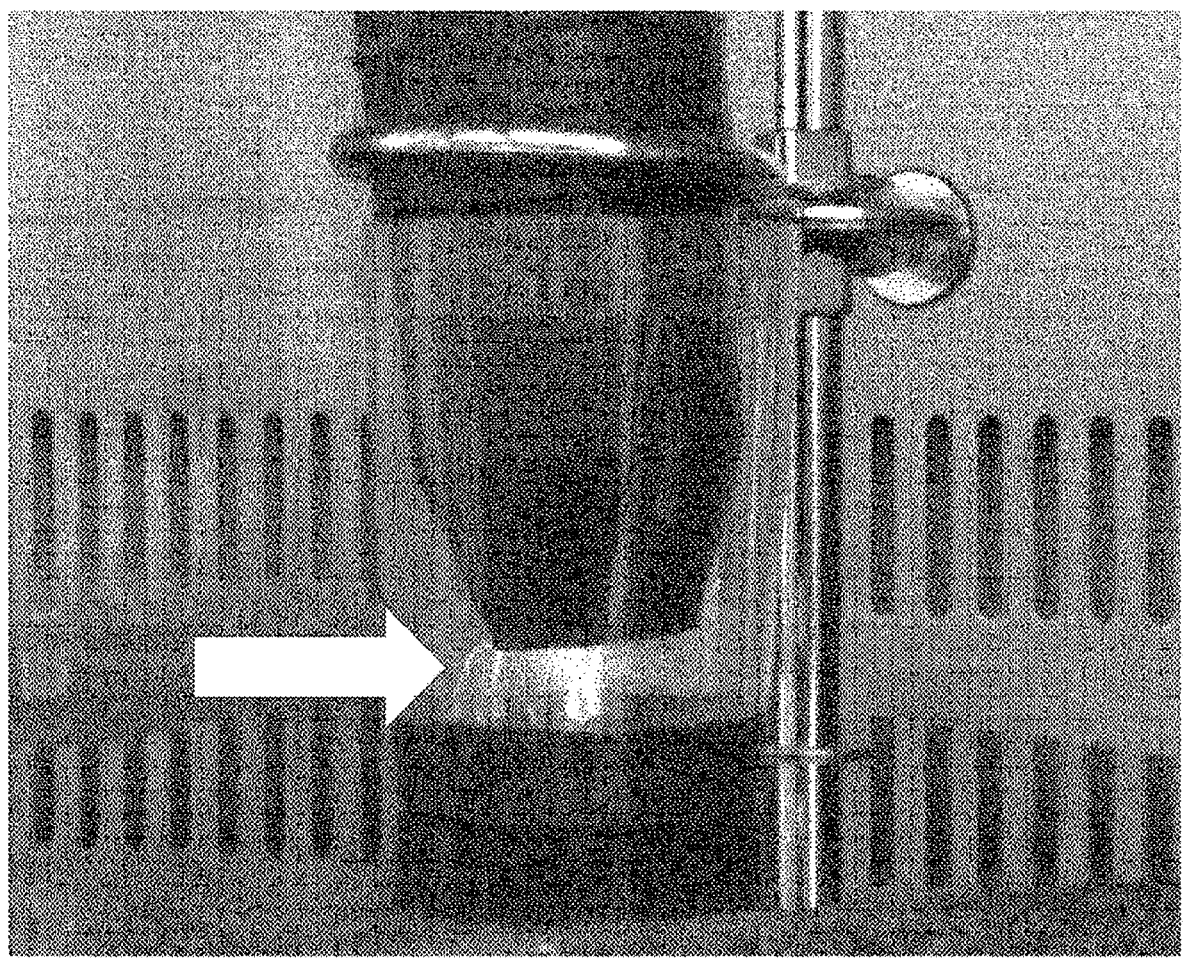
FIGS. 1A and 1B illustrate a method of preparing liquid-type plasma (nonthermal plasma treated solution, NTS) according to the present invention.

10 ml of F12 (10% FBS 24 ug/ml 3-isobutyl-1-methylxanthine, 80 nM 12-O-tetradecanoyl Phorbor 13-acetate (TPA), 1.2 g/ml bFGF, 0.1 ug/ml cholera toxin) was placed in a container to prepare a culture medium. The culture medium was treated with plasma at an intensity of 4 KV under a condition of 1 minute per ml at a distance 1 cm spaced apart from the culture medium using helium and oxygen as carrier gases, thus preparing liquid-type plasma ("plasma-treated culture medium"). A method of preparing the liquid-type plasma is illustrated in FIG. 1A.

Figure 1B:
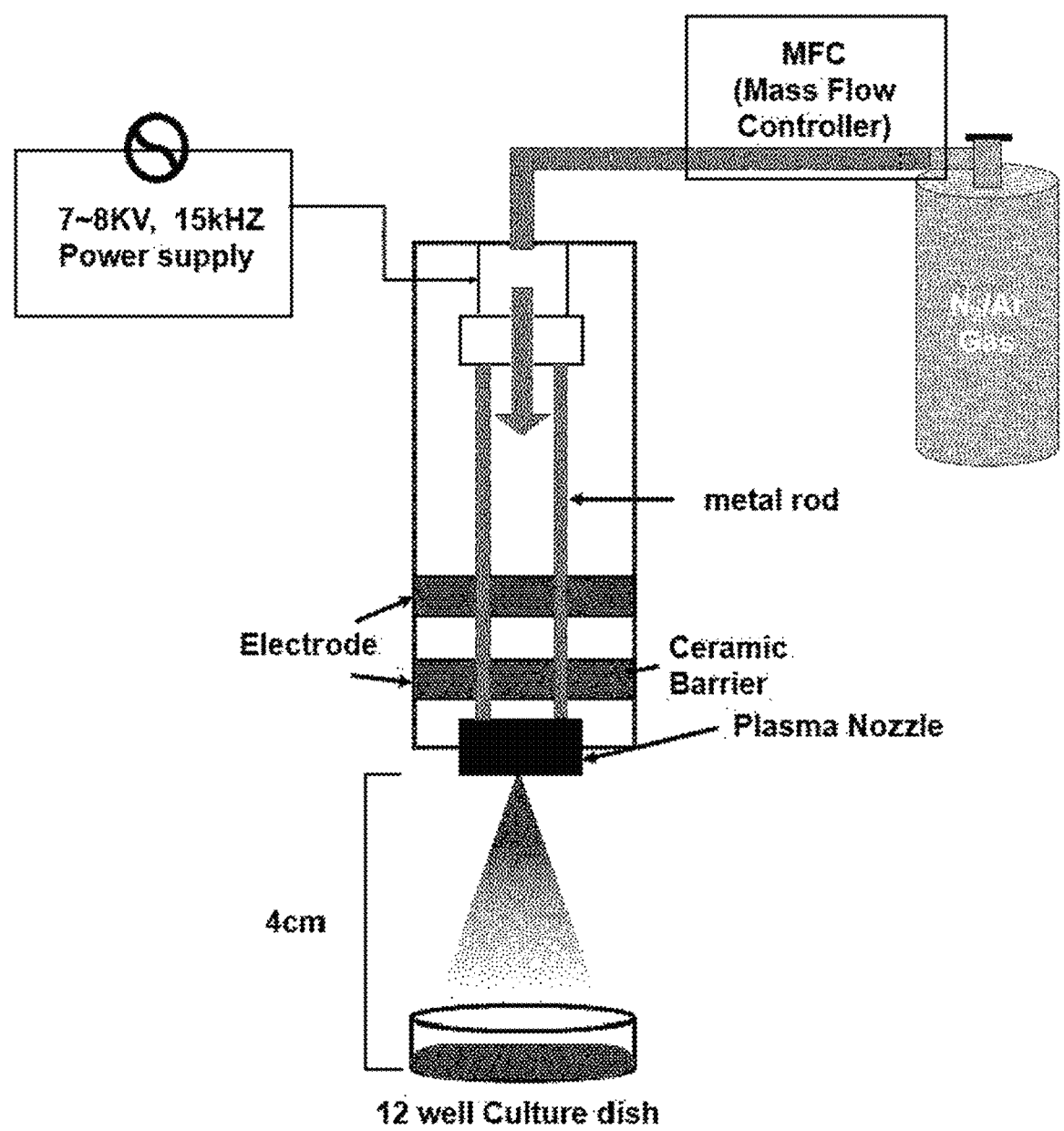

Example 1-2. Preparation of Composition Including Liquid-Type Plasma (NTS) and Growth Factor To investigate an effect of the liquid-type plasma according to the present invention and a growth factor on wound treatment, cell migration in fibroblasts was evaluated using DMEM High Glucose+10% FBS, as a culture medium, and EGF, as a growth factor. First, power having a voltage of 15 kV and a frequency 15 kHz was supplied. The culture medium was treated with plasma by means of a plasma generator using nitrogen gas as a carrier gas, thus preparing liquid-type plasma ("plasma-treated culture medium"). A method of preparing the liquid-type plasma is illustrated in FIG. 1B.

Example 2. Investigation of Effect of Liquid-Type Plasma on Skin Whitening

Example 2-1. Pigmentation Inhibition Effect in Zebrafish

Embryos collected from zebrafish were placed in a zebrafish embryo culture medium (egg water, 0.2 g sea salt/L) and were allowed to develop for 24 hours, followed by being treated with the liquid-type plasma prepared according to Example 1. To increase the penetration of the sample into chorions during sample processing, chorions of the embryos were pierced with tweezers. 24 hours after the sample treatment, embryos showing toxicity were removed. Chorions of the remaining embryos were completely removed, and then the chorion-removed embryos were treated at the same concentration. 48 hours after the treatment, the degrees of pigmentation in the treated samples, compared to a control, were observed with a stereomicroscope. Results are shown in FIG. 2.

Figure 2:
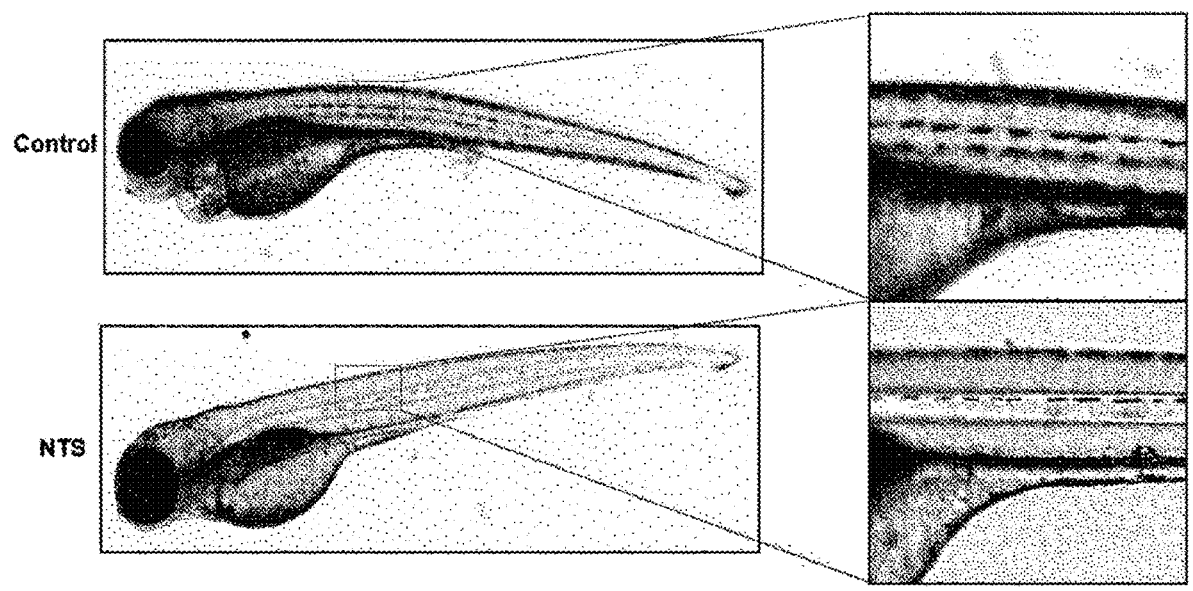
FIG. 2 illustrates a pigmentation inhibition effect of liquid-type plasma according to the present invention in Zebrafish.

Referring to FIG. 2, it was confirmed that, in the case of the zebrafish treated with the liquid-type plasma, pigmentation is inhibited compared to a control.

Example 2-2. Pigmentation Inhibition Effect in Human Skin Tissue

Human foreskin tissue was cultured in Transwell (DMEM high glucose+4% FBS), and then was treated with the liquid-type plasma prepared according to Example 1 at a rate of 1 min/1 ml. After incubation for 3 days, the human foreskin tissue was fixed and a pigmentation degree thereof was observed through Fontana-Masson staining. Results are shown in FIG. 3.

Figure 3:
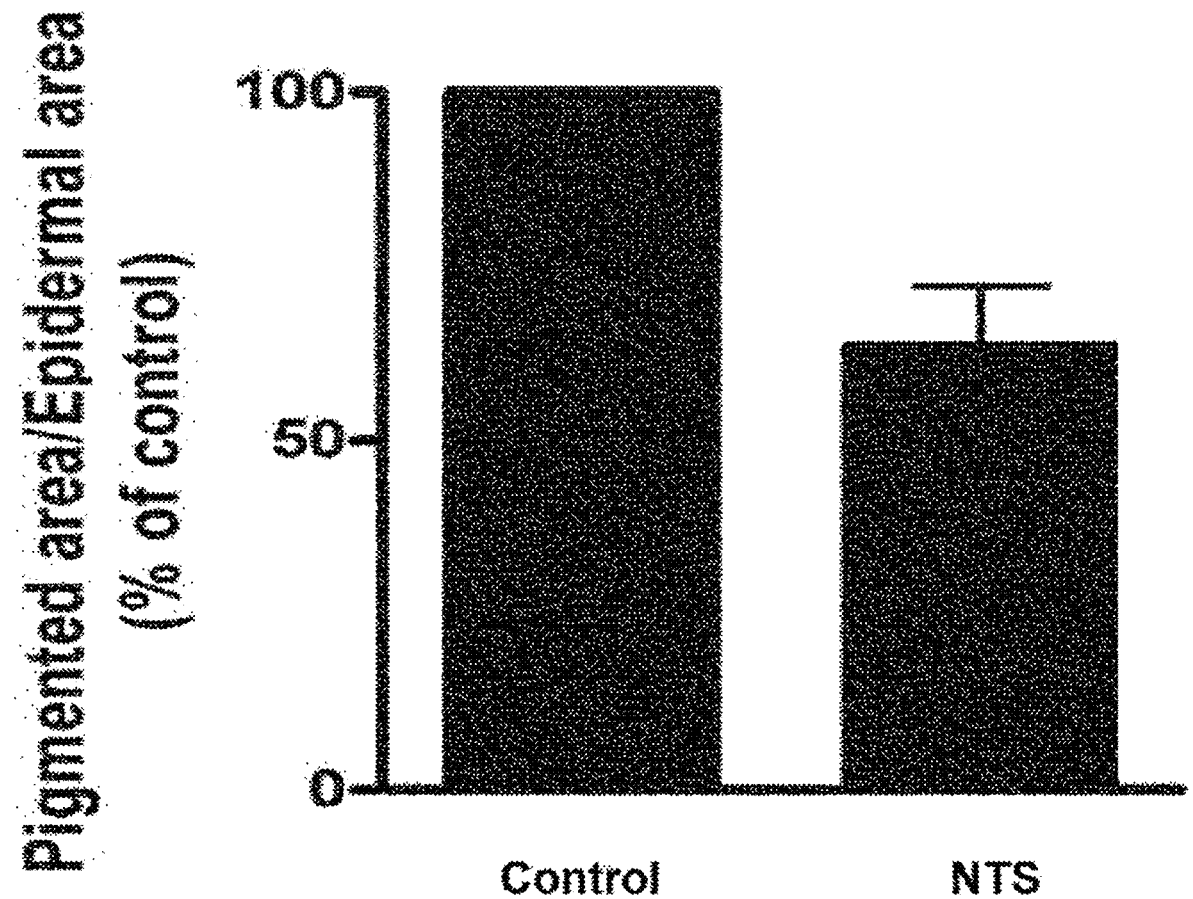
FIG. 3 illustrates a pigmentation inhibition effect of liquid-type plasma according to the present invention in human skin tissue.

Referring to FIG. 3, it was confirmed that epidermal staining in the human skin tissue treated with the liquid-type plasma was weaker than that in a control.

Figure 4A:
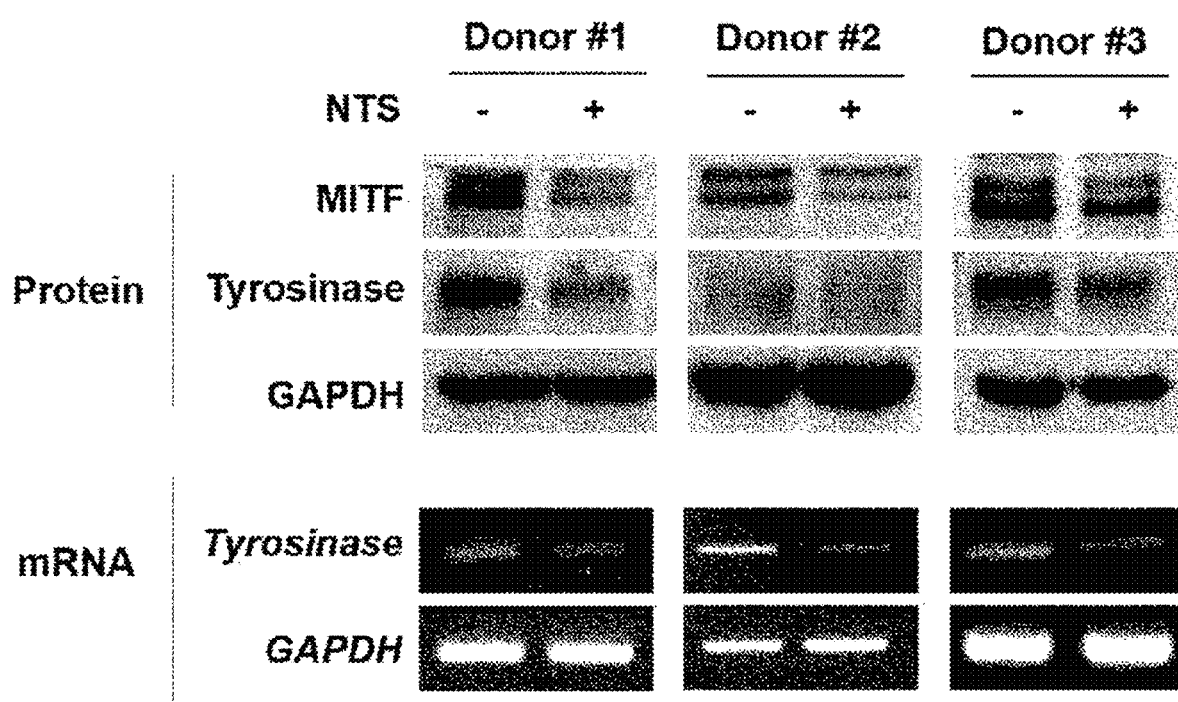
FIGS. 4A and 4B illustrate a tyrosinase activity inhibition effect of liquid-type plasma according to the present invention in human skin tissue.
Figure 4B:
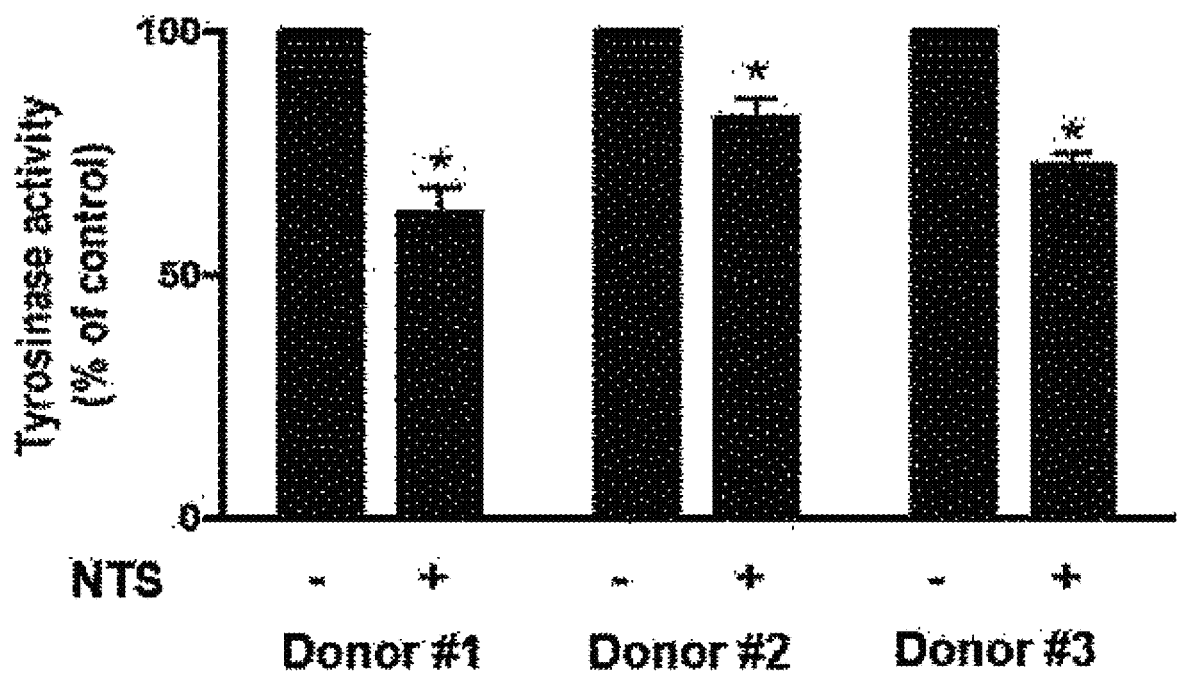

Example 2-3. Tyrosinase Activity Inhibition Effect in Human Skin Tissue $2 \times 10^6$ of a human foreskin sample was seeded in a 60 mm dish, and then treated with the liquid-type plasma prepared according to Example 1 at a rate of 1 min/1 ml. After incubation for 24 hours and fixation, Western blotting and PCR analysis were performed and tyrosinase activity and melanin content were measured. Results are shown in FIGS. 4A and 4B.

Figure 4B:
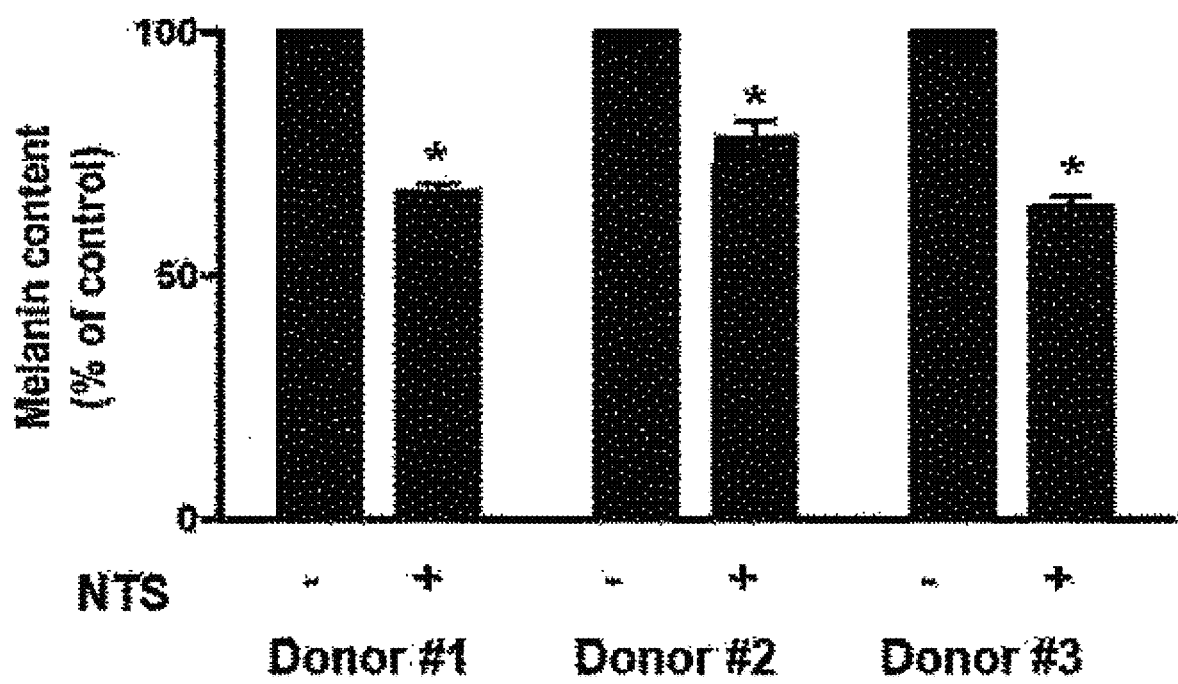

As shown in FIG. 4, it was confirmed that tyrosinase, MITF, and melanin content were significantly reduced in the human skin tissue treated with the liquid-type plasma.

Example 2-4. Toxicity Evaluation in Melanocytes

Human melanocytes were treated with the liquid-type plasma prepared according to Example 1, and then cytotoxicity thereof was observed over time. Results are shown in FIG. 5.

Figure 5:
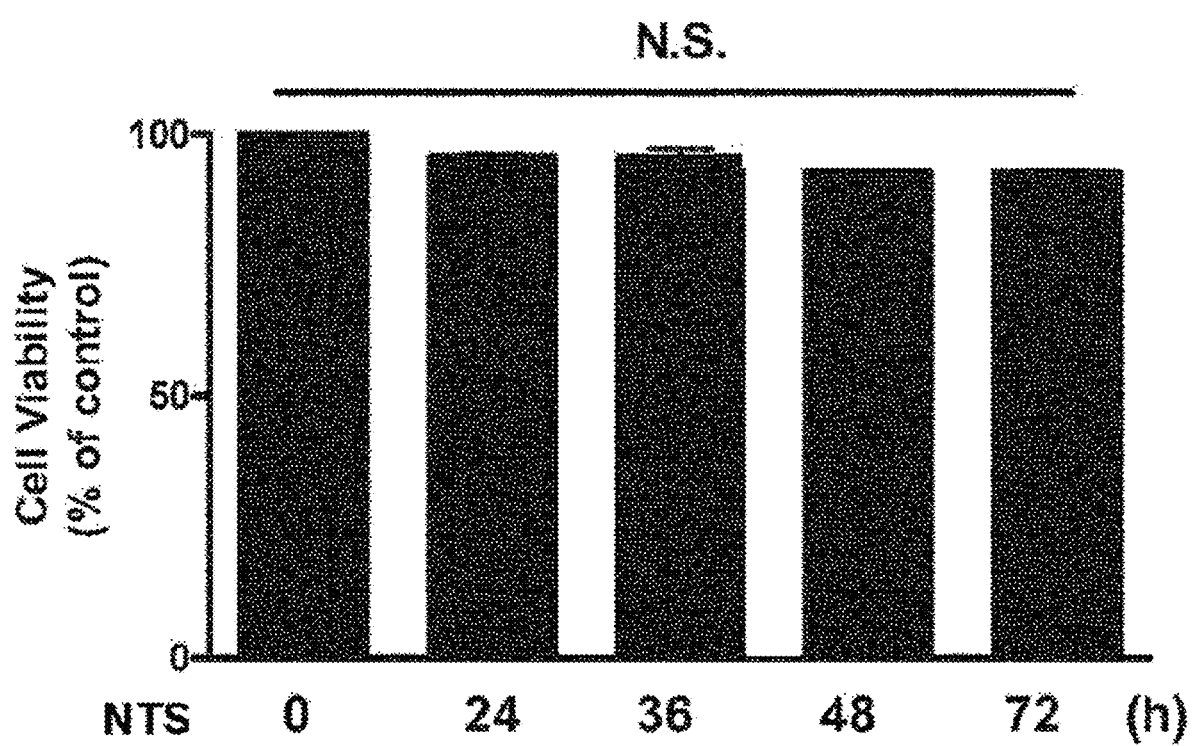
FIG. 5 illustrates toxicity test results of liquid-type plasma according to the present invention in melanocytes.

As shown in FIG. 5, it was confirmed that the liquid-type plasma according to the present invention did not exhibit toxicity in the human melanocyte.

Example 2-5. Melanogenesis Marker Reduction Effect in Human Melanocytes

Figure 6A:
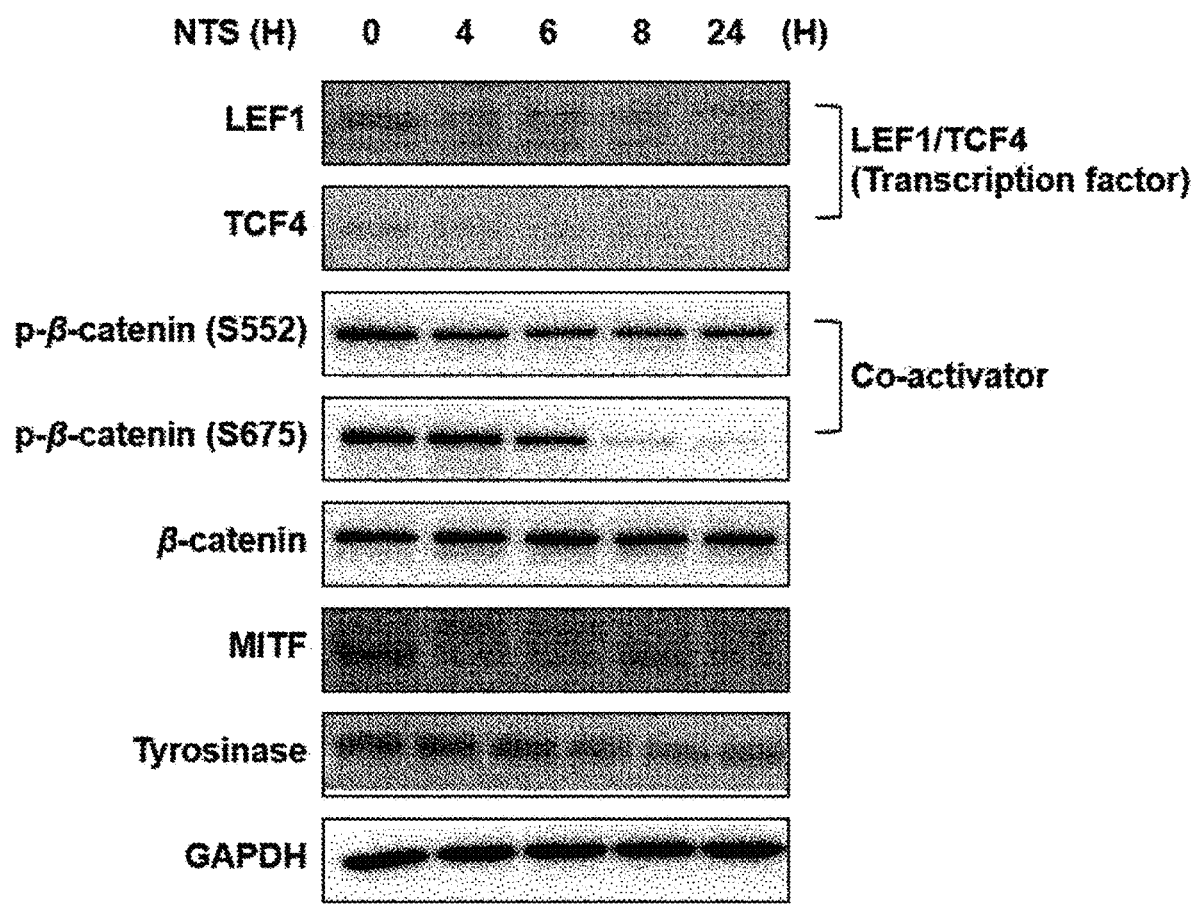
FIGS. 6A and 6B illustrate a melanogenesis marker reduction effect of liquid-type plasma according to the present invention in human melanocytes.
Figure 6B:
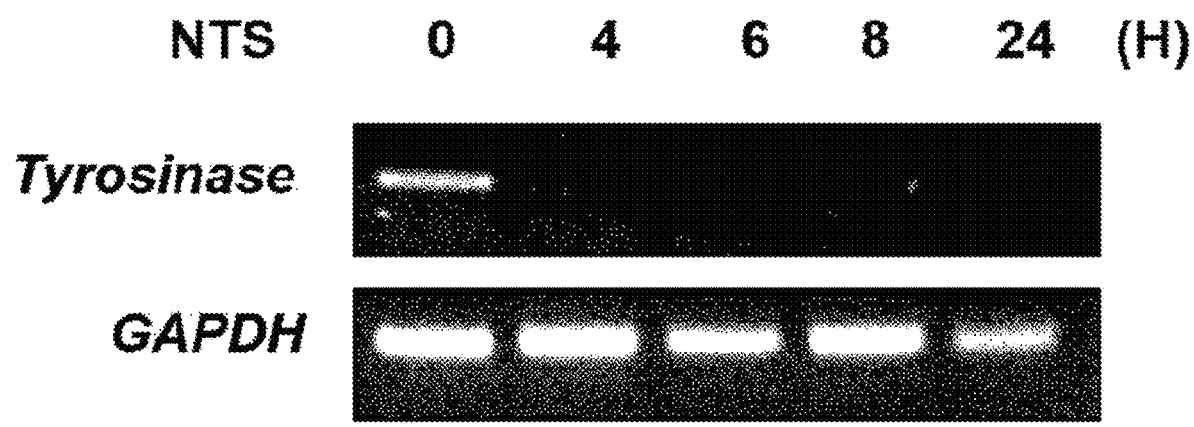

Human melanocytes were treated with the liquid-type plasma prepared according to Example 1, and reduction of melanogenesis markers in the human melanocytes was observed over time. Results are shown in FIGS. 6A and 6B.

As shown in FIG. 6, it was confirmed that the liquid-type plasma according to the present invention had a reduction effect on melanogenesis markers in the human melanocyte. Here, an RNA level of tyrosinase as well as protein levels of the melanogenesis markers were reduced.

Example 3. Evaluation of Wound Treatment Effect of Liquid-Type Plasma

Example 3-1. Wound Treatment Effect Evaluation

The liquid-type plasma prepared according to Example 1 was pretreated with each of 10 ng/ml and 30 ng/ml of EGF, and a human-derived fibroblast line ($1 \times 10^5$ cells) were seeded therein. After 1 hour, migration of the cells was evaluated by wound healing assay.

Meanwhile, as comparative examples, fibroblasts were seeded in each of liquid-type plasma and EGF, and then migration of the fibroblasts therein was observed. Results are shown in FIG. 7.

Figure 7:
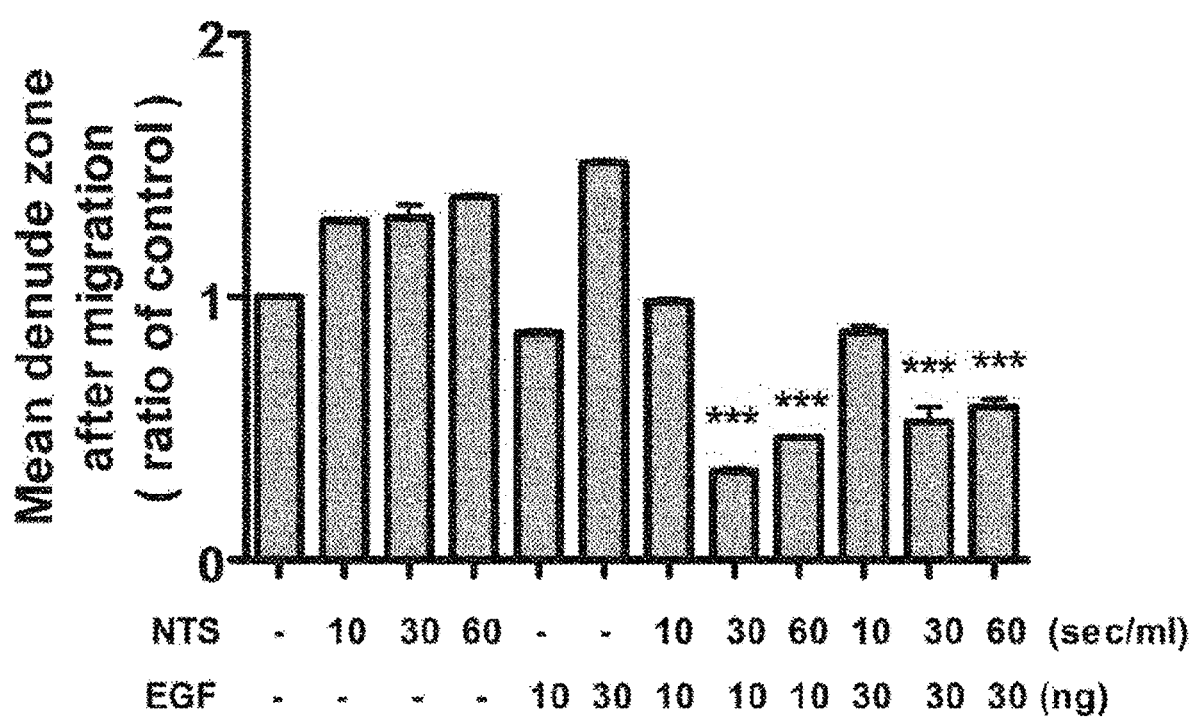
FIG. 7 illustrates a wound treatment effect of liquid-type plasma according to the present invention.

Referring FIG. 7, in the comparative examples, a wound treatment effect was not exhibited in the group treated with only the liquid-type plasma, but was exhibited in the group treated with only EGF. In the group treated with both the liquid-type plasma and EGF, the wound treatment effect was significant, compared to the group treated with only EGF.

Example 3-2. Cytotoxicity Investigation

To investigate whether the composition containing including the liquid-type plasma according to the present invention and EGF exhibited cytotoxicity against fibroblasts, the viability of the fibroblasts was evaluated by MTT. Results are shown in FIG. 8.

Figure 8:
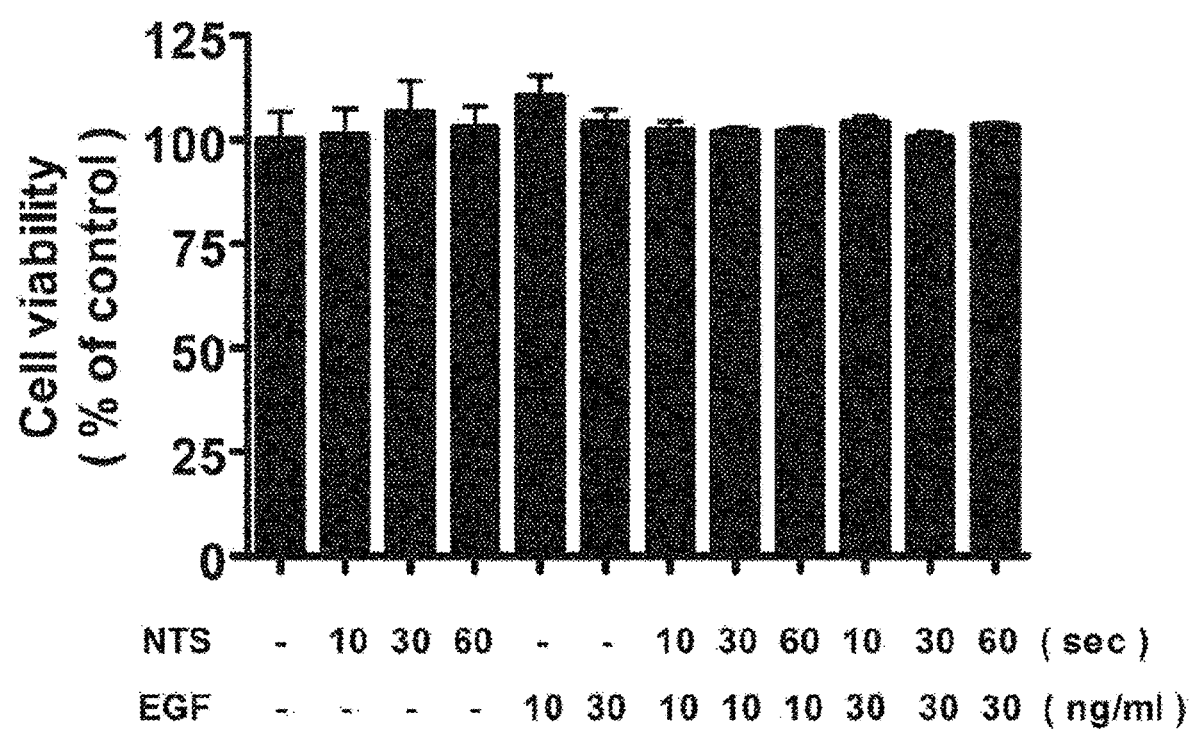
FIG. 8 illustrates cytotoxicity test results of liquid-type plasma according to the present invention.

Referring to FIG. 8, it was confirmed that the composition according to the present invention did not exhibit cytotoxicity against fibroblasts.

While this invention has been particularly shown and described with reference to preferred embodiments thereof, it will be understood by those skilled in the art that various changes in form and details may be made therein without departing from the spirit and scope of the invention as defined by the appended claims. The preferred embodiments should be considered in descriptive sense only and not for purposes of limitation. Therefore, the scope of the invention is defined not by the detailed description of the invention but by the appended claims, and all differences within the scope of equivalents will be construed as being included in the present invention.

INDUSTRIAL APPLICABILITY

A composition containing liquid-type plasma as an active ingredient according to the present invention exhibits an excellent skin whitening effect and an excellent treatment or prevention effect on skin pigmentation diseases.

In addition, a composition including the liquid-type plasma and a growth factor of the present invention can induce the proliferation of fibroblasts, thereby exhibiting excellent wound treatment efficacy. Accordingly, the composition according to the present invention can be usefully applied to external preparations for wound treatment, medicines, and the like.

The invention claimed is:

1. A method of preventing or treating skin pigmentation diseases, the method comprising administering a liquid type plasma as an active ingredient to a subject,
   wherein the skin pigmentation diseases are one or more selected from the group consisting of melasma, freckles, a lentigo, a nevus, drug-induced pigmentation, post-inflammatory pigmentation, and hyperpigmentation caused by dermatitis; and
   wherein the liquid type plasma is prepared by a method comprising:
   (a) a step of filling a plasma generator with a carrier gas that is nitrogen;
   (b) a step of supplying a voltage of 15 kV and a frequency of 15 kHz to the plasma generator to generate plasma; and
   (c) a step of irradiating a liquid material that is a cell culture minimum medium with the generated plasma, wherein the cell culture minimum medium (i) is present within a container during the irradiation and (ii) comprises a carbon source, a nitrogen source, and trace element components.

2. A method of treating a wound, the method comprising administering a liquid type plasma as an active ingredient to a subject; and
   wherein the liquid type plasma is prepared by a method comprising:
   (a) a step of filling a plasma generator with a carrier gas that is nitrogen;
   (b) a step of supplying a voltage of 15 kV and a frequency of 15 kHz to the plasma generator to generate plasma; and
   (c) a step of irradiating a liquid material that is a cell culture minimum medium with the generated plasma, wherein the cell culture minimum medium (i) is present within a container during the irradiation and (ii) comprises a carbon source, a nitrogen source, and trace element components.

3. The method according to claim 2, wherein the liquid type plasma is pretreated with a growth factor.

4. The method according to claim 3, wherein the growth factor is an epidermal growth factor (EGF), platelet-derived growth factor-AA (PDGF-AA), insulin-like growth factor-1 (IGF-1), transforming growth factor-β (TGF-β), or a fibroblast growth factor (FGF).

5. The method according to claim 2, wherein the wound is a puncture wound, decortication, a rash, inflammation, an ulcer, or a skin injury due to scratches.

6. The method according to claim 1, wherein the cell culture minimum medium is selected from the group consisting of Dulbecco's Modified Eagle's Medium (DMEM), Minimal Essential Medium (MEM), Basal Medium Eagle (BME), RPMI1640, F-10, F-12, Glasgow's Minimal essential Medium (GMEM), and Iscove's Modified Dulbecco's Medium.

7. The method according to claim 2, wherein the cell culture minimum medium is selected from the group consisting of Dulbecco's Modified Eagle's Medium (DMEM), Minimal Essential Medium (MEM), Basal Medium Eagle (BME), RPMI1640, F-10, F-12, Glasgow's Minimal essential Medium (GMEM), and Iscove's Modified Dulbecco's Medium.

* * * * *